(12) United States Patent
Davies

(10) Patent No.: US 7,091,040 B1
(45) Date of Patent: Aug. 15, 2006

(54) P450/ACETAMINOPHEN GENETICALLY DIRECTED ENZYME PRODRUG THERAPY (GDEPT)

(75) Inventor: Donald Davies, Buckinghamshire (GB)

(73) Assignee: Innovata PLC, Nottingham (GB)

( * ) Notice: Subject to any disclaimer, the term of this patent is extended or adjusted under 35 U.S.C. 154(b) by 0 days.

(21) Appl. No.: 09/869,696

(22) PCT Filed: Dec. 30, 1999

(86) PCT No.: PCT/GB99/04268

§ 371 (c)(1),
(2), (4) Date: Oct. 31, 2001

(87) PCT Pub. No.: WO00/40271

PCT Pub. Date: Jul. 13, 2000

(30) Foreign Application Priority Data

Jan. 4, 1999 (GB) ................................. 9900009.3
Sep. 4, 1999 (GB) ................................. 9920837.3

(51) Int. Cl.
C12N 15/63 (2006.01)
C12N 15/74 (2006.01)
C12N 9/00 (2006.01)
A61K 31/70 (2006.01)
C07H 21/02 (2006.01)
A01N 63/00 (2006.01)

(52) U.S. Cl. .................... 435/455; 435/320.1; 435/325; 435/183; 514/44; 536/23.1; 536/24.1; 424/93.2; 424/93.21

(58) Field of Classification Search ............. 424/93.21, 424/93.2, 93.1; 435/320.1, 325, 455; 514/44
See application file for complete search history.

(56) References Cited

U.S. PATENT DOCUMENTS 5,760,008 A 6/1998 Rubin

2003/0158137 A1 * 8/2003 Davies ........................ 514/44

OTHER PUBLICATIONS

Verma, I.M. and Somia, N. Gene Therapy- promises, problems and prospect. Sep., 1997. Nature, vol. 389, pp. 239-242.*
Russell, S.J. Replicating Vectors for Gene Therapy of Cancer: Risks, Limitations and Prospects. 1994. European J. of Cancer vol. 30(A). pp. 1165-1171.*
Meng R.D. and El-Deiry, W.S. Tumor Suppressor Genes as Targets for Cancer Gene Therapy. 1999. Gene Therapy of Cancer,Chapter 1. pp. 3-18.*
Marshall, E. Second Child In French Trial Is Found to Have Leukemia. Jan. 17, 2003. Science vol. 299, p. 320.*
Gura, T, Systems for identifiying New Drugs Are Often Faulty, Science, 1997, vol. 2788, pp. 1041-1042.*
Palmer et al, Inhibition of NK-kB enhances the cytotoxicity of virus-directed enzyme prodrug therapy and ocnolytic adenovirus cancer gene therapy, Gene Therapy, 2005, vol. 12, p. 1187-1197.*
Database Biosis, Biosciences Information Service Abstract of "Divergent Effects of Intravenous GSH and Cysteine on Renal and Hepatic GSH". No. XP002140944.
Database Biosis, Biosciences Information Service Abstract of "Cellular Thiols in Rat Liver Cell Lines Possessing Different Growth Characteristics". No. XP002140945.
Database Biosis, Biosciences Information Service Abstract of "Glutathione levels and variability in breast tumors and normal tissue." No. XP002140946.
Database Biosis, Biosciences Information Service Abstract of "Cytochrome P450 enzymes involved in acetaminophen activation by rat and human liver microsomes and their kinetics". No. XP002140947.

* cited by examiner

Primary Examiner—Dave Trong Nguyen
Assistant Examiner—Maria Marvich
(74) Attorney, Agent, or Firm—Crowell & Moring LLP

(57) ABSTRACT

The invention hereindescribed relates to a form of cancer therapy which exploits the cytotoxic properties of acetaminophen when converted to NABQI by the metabolic activity of tumour cell specific P450; vectors for use in the delivery of P450 to tumour cells; and therapeutic compositions comprising said vectors.

39 Claims, 6 Drawing Sheets

FIGURE 6

```
GTTTGACAGCTTATCATCGACTGCACGGTGCACCAATGCTTCTGGCGTCAGGCAGCCATCGGAAGCTGTGGTATGGCTGT
GCAGGTCGTAAATCACTGCATAATTCGTGTCGCTCAAGGCGCACTCCCGTTCTGGATAATGTTTTTTGCGCCGACATCAT
AACGGTTCTGGCAAATATTCTGAAATGAGCTGTTGACAATTAATCATCGGCTCGTATAATGTGTGGAATTGTGAGCGGA
TAACAATTTCACACAGGAAACAGACCATGGAGCAGAAGCTGATTTCCGAGGAGGACCTGGGATCCGAATTCAAGCTTCCC
GGGGTCGACATCGATTAGACTAGTCTAGACGGCGGCGGCAGCTTGGCTGTTTTGGCGGATGAGAGAAGATTTTCAGCCTG
ATACAGATTAAATCAGAACGCAGAAGCGGTCTGATAAAACAGAATTTGCCTGGCGGCAGTAGCGCGGTGGTCCCACCTGA
CCCCATGCCGAACTCAGAAGTGAAACGCCGTAGCGCCGATGGTAGTGTGGGGTCTCCCCATGCGAGAGTAGGGAACTGCC
AGGCATCAAATAAAACGAAAGGCTCAGTCGAAAGACTGGGCCTTTCGTTTTATCTGTTGTTTGTCGGTGAACGCTCTCCT
GAGTAGGACAAATCCGCCGGGAGCGGATTTGAACGTTGCGAAGCAACGGCCCGGAGGGTGGCGGGCAGGACGCCCGCCAT
AAACTGCCAGGCATCAAATTAAGCAGAAGGCCATCCTGACGGATGGCCTTTTTGCGTTTCTACAAACTCTTTTTGTTTAT
TTTTCTAAATACATTCAAATATGTATCCGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTTGCCTTCCTGTTTTTGCTCACCCAGA
AACGCTGGTGAAAGTAAAAGATGCTGAAGATCAGTTGGGTGCACGAGTGGGTTACATCGAACTGGATCTCAACAGCGGTA
AGATCCTTGAGAGTTTTCGCCCCGAAGAACGTTTTCCAATGATGAGCACTTTTAAAGTTCTGCTATGTGGCGCGGTATTA
TCCCGTGTTGACGCCGGGCAAGAGCAACTCGGTCGCCGCATACACTATTCTCAGAATGACTTGGTTGAGTACTCACCAGT
CACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGC
CTTGATCGTTGGGAACCGGAGCTGAATGAAGCCATACCAAACGACGAGCGTGACACCACGATGCCTACAGCAATGGCAAC
AACGTTGCGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATAATCTC
ATGACCAAAATCCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTCCTTCTAGTGTAGCCGTAG
TTAGGCCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCTGGCCTTTTGCTCAC
ATGTTCTTTCCTGCGTTATCCCCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCTGATGCGGTATTTTCTCCTTACGCATCTGT
GCGGTATTTCACACCGCATATGGTGCACTCTCAGTACAATCTGCTCTGATGCCGCATAGTTAAGCCAGTATACACTCCGC
TATCGCTACGTGACTGGGTCATGGCTGCGCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCAGAGGTTTTCACCGTCATCACCGAAACG
    CGCGAGGCAGCAGATCAATTCGCGCGCGAAGGCGAAGCGGCATGCATTTACGTTGACACCATCGAATGGTGCAAAACCTT
    TCGCGGTATGGCATGATAGCGCCCGGAAGAGAGTCAATTCAGGGTGGTGAATGTGAAACCAGTAACGTTATACGATGTCG
    CAGAGTATGCCGGTGTCTCTTATCAGACCGTTTCCCGCGTGGTGAACCAGGCCAGCCACGTTTCTGCGAAAACGCGGGAA
    AAAGTGGAAGCGGCGATGGCGGAGCTGAATTACATTCCCAACCGCGTGGCACAACAACTGGCGGGCAAACAGTCGTTGCT
    GATTGGCGTTGCCACCTCCAGTCTGGCCCTGCACGCGCCGTCGCAAATTGTCGCGGCGATTAAATCTCGCGCCGATCAAC
    TGGGTGCCAGCGTGGTGGTGTCGATGGTAGAACGAAGCGGCGTCGAAGCCTGTAAAGCGGCGGTGCACAATCTTCTCGCG
    CAACGCGTCAGTGGGCTGATCATTAACTATCCGCTGGATGACCAGGATGCCATTGCTGTGGAAGCTGCCTGCACTAATGT
    TCCGGCGTTATTTCTTGATGTCTCTGACCAGACACCCATCAACAGTATTATTTTCTCCCATGAAGACGGTACGCGACTGG
    GCGTGGAGCATCTGGTCGCATTGGGTCACCAGCAAATCGCGCTGTTAGCGGGCCCATTAAGTTCTGTCTCGGCGCGTCTG
    CGTCTGGCTGGCTGGCATAAATATCTCACTCGCAATCAAATTCAGCCGATAGCGGAACGGGAAGGCGACTGGAGTGCCAT
    GTCCGGTTTTCAACAAACCATGCAAATGCTGAATGAGGGCATCGTTCCCACTGCGATGCTGGTTGCCAACGATCAGATGG
    CGCTGGGCGCAATGCGCGCCATTACCGAGTCCGGGCTGCGCGTTGGTGCGGATATCTCGGTAGTGGGATACGACGATACC
    GAAGACAGCTCATGTTATATCCCGCCGTTAACCACCATCAAACAGGATTTTCGCCTGCTGGGGCAAACCAGCGTGGACCG
    CTTGCTGCAACTCTCTCAGGGCCAGGCGGTGAAGGGCAATCAGCTGTTGCCCGTCTCACTGGTGAAAAGAAAAACCACCC
    TGGCGCCCAATACGCAAACCGCCTCTCCCCGCGCGTTGGCCGATTCATTAATGCAGCTGGCACGACAGGTTTCCCGACTG
    GAAAGCGGGCAGTGAGCGCAACGCAATTAATGTGAGTTAGCGCGAATTGATCTG
```

US 7,091,040 B1

P450/ACETAMINOPHEN GENETICALLY DIRECTED ENZYME PRODRUG THERAPY (GDEPT)

1. FIELD OF THE INVENTION

This invention relates to a form of gene therapy known as genetically directed enzyme prodrug therapy (GDEPT).

2. BACKGROUND OF THE INVENTION

Current therapies to treat cancer involve, amongst other things, radiation therapy and chemotherapy each of which, although effective at retarding the growth of cancer cells, have significant disadvantages since each treatment is typically selective for cells that are actively dividing. Consequently, normal dividing cells are also destroyed resulting in significant undesirable side effects, such as nausea and immunosupression, the latter of which can lead to complications of secondary infections. In recent years research has focussed on providing selective treatments which lessen these undesirable side effects. One such therapy is GDEPT[1,2].

GDEPT is of particular interest with respect to the treatment of cancer in that it offers advantages over conventional chemotherapeutic methods of cancer treatment. In such conventional methods the drugs administered to the patient attack not only the targeted cancer cells but also normal cells. Destruction of cancer cells is achieved at the expense of inflicting damage on normal cells, creating serious side-effects. In treatment of cancer by GDEPT the objective is to create an anti-cancer drug in situ within the cancer cell while creating little or none in normal cells, thereby attacking the cancer cells while leaving the normal cells substantially unaffected. This is typically achieved by administration to the patient of a vector containing a gene for an enzyme which can convert a relatively non-toxic substance (commonly referred to as a prodrug) into a cytotoxic agent. The vector also contains a promoter, ie a DNA sequence constituting a switch for the gene, this promoter being responsive to a regulatory protein found solely in the cancer cells or to a greater extent in the cancer cells than in normal cells. The gene is thus expressed substantially in the cancer cells so it is only (or mainly) in the cancer cells that the enzyme is produced and that conversion of the prodrug to the cytotoxic agent takes place. Formation of the cytotoxic agent therefore takes place primarily in the cancer cells. In this way the cancer cells are selectively attacked, with relatively little damage to normal cells.

In one example of the use of GDEPT in cancer treatment, the prodrug is 5-fluoro-cytosine (5-FC). 5-FC is itself relatively non-toxic to human cells but can be converted into a potent anti-cancer drug, 5-fluorouracil (5-FU), by the enzyme cytosine deaminase. A bacterial gene which expresses cytosine deaminase is incorporated in a viral vector in association with a promoter which is responsive to a regulatory protein that is characteristic of the particular type of cancer cell under attack. For instance, in treating breast cancer the promoter could be one which is responsive to the regulatory protein EBB2 or in treating liver cancer one which is responsive to α-fetoprotein.

In known GDEPT techniques, difficulty has been encountered in achieving as high a degree of selectivity as is desirable, (ie in destroying cancer cells while limiting the damage to normal cells). This is at least partly due to the fact that normal cells may come under attack from cytotoxic agents which have been formed in the cancer cells but have found their way out of those cells, for example when the cells break down under the cytotoxic action of the drug.

In addition, some chemotherapeutic agents are selective for particular cell-cycle phases (eg G1, S, G2 or mitosis). It is desirable to provide chemotherapeutic agents that are not so restricted in their effects and can kill cells irrespective of the cell-cycle stage.

3. DETAILED BACKGROUND OF THE INVENTION

3.1. Acetaminophen as a Prodrug

Acetaminophen is a widely used mild pain reliever and antipyretic. However, it is a potentially dangerous drug in that an overdose of it can cause serious, even fatal, damage to the liver[3]. This is due to the fact that liver cells express a gene for a P450 enzyme, specifically CYP1A2, also to a much lesser extent CYP 2E1 and CYP 3A4. This enzyme can convert acetaminophen into a metabolite, N-acetylbenzoquinoneimine (NABQI), which is highly cytotoxic. For standard dosages of acetaminophen, the toxicity of NABQI is countered in the liver by conversion of NABQI into a non-toxic substance by reaction with glutathione, a normal component of human cells[4,5]. The supply of glutathione is however insufficient to deal with the large amounts of NABQI formed in liver cells after an overdose of acetaminophen and the cells are therefore then damaged or destroyed.

When acetaminophen constitutes the prodrug in GDEPT, the vector administered contains a gene for a p450 enzyme[7,8], preferably CYP1A2, and the cytotoxic agent formed in the cancer cells is NABQI. In contrast to other cytotoxic agents, NABQI causes little or no systemic toxicity.

3.2 Tumour Specific Gene Expression

It might have been expected that the use of acetaminophen as a prodrug in GDEPT would be impractical. Selective expression of the gene for the enzyme CYP1A2 in cancer cells could be effected by administration of a vector containing that gene in association with a promoter which is responsive to a regulatory protein found only in the cancer cells. The enzyme CYP1A2, created as a result of the entry into cells of that vector, would then convert acetaminophen into NABQI in the cancer cells and damage or destroy them. As in conventional GDEPT using prodrugs other than acetaminophen, selectivity between cancer cells and normal cells would be achieved because entry of the vector into normal cells would not cause expression of the CYP1A2 gene contained in the vector since the normal cells do not contain the regulatory protein which activates the chosen promoter for the gene. In general, the normal cells would therefore not contain the enzyme CYP1A2 and would be unaffected by the presence of acetaminophen because in such cells it would not undergo intracellular conversion to NABQI. However, as mentioned above, normal liver cells naturally express a gene for CYP1A2. It would therefore be expected that administering a dose of acetaminophen high enough to create a level of NABQI in cancer cells capable of killing such cells could also result in the creation of sufficient NABQI in the normal liver cells to kill them too. Surprisingly, this is not so, probably due to a difference in the glutathione content of normal liver cells and that of cancer cells. It appears that most cancer cells may contain only about one-fifth of the glutathione present in normal liver cells. The concentration of the cytotoxic NABQI is therefore kept much lower in the normal liver cells than in the cancer cells because more NABQI can be detoxified, by combination of NABQI with glutathione, in the normal liver cells than in the cancer cells.

3.4 Gene Therapy Vectors & P450 Genes

The vector used in the present invention is one containing a gene for a p450 enzyme, preferably for CYP1A2, and a promoter which acts as a switch for that gene and which is responsive to a regulator protein characteristic of the type of cancer being addressed. The gene can be derived from human DNA (Ikeyak et al Molecular Endocrinology (1989), 3: 1399–1408). However, it may be advantageous to use a P450 gene derived from non-human DNA, for example mouse DNA or hamster DNA. The P450 enzyme generated by the mouse gene is relatively unaffected by certain compounds, for example furaphylline, which act as inhibitors of the form of the enzyme CYP1A2 generated by the human gene. Administration of such inhibitors makes it possible to raise the dosage of acetaminophen above the normally safe dosage; an inhibitor such as furaphylline can protect the normal liver cells by inhibiting the form of P450 generated by expression in those cells of the human gene, while having little or no effect on the form of P450 generated by expression of the mouse gene in the cancer cells. The level of NABQI in the normal liver cells is therefore diminished by such inhibitors while the level of NABQI in the cancer cells is relatively unaffected by the inhibitors.

With regard to non-viral delivery, synthetic uptake of DNA into mammalian cells can be facilitated by condensing it with lipids, proteins or peptides. These include, by example and not by way of limitation, polymers, dendrimers and cationic lipid delivery means (eg liposomes).

Liposomes are lipid based vesicles which encapsulate a selected therapeutic agent which is then introduced into a patient. The liposome is manufactured either from pure phospholipid or a mixture of phospholipid and phosphoglyceride. Typically liposomes can be manufactured with diameters of less than 200 nm, this enables them to be intravenously injected and able to pass through the pulmonary capillary bed. Furthermore the biochemical nature of liposomes confers permeability across blood vessel membranes to gain access to selected tissues. Liposomes do have a relatively short half-life. So called STEALTH$^R$ liposomes have been developed which comprise liposomes coated in polyethylene glycol (PEG). The PEG treated liposomes have a significantly increased half-life when administered intravenously to a patient. In addition STEALTH$^R$ liposomes show reduced uptake in the reticuloendothelial system and enhanced accumulation selected tissues. In addition, so called immuno-liposomes have been develop which combine lipid based vesicles with an antibody or antibodies, to increase the specificity of the delivery of the DNA vector to a selected cell/tissue.

The use of liposomes as delivery means is described in U.S. Pat. No. 5,580,575 and U.S. Pat. No. 5,542,935.

Bacteria such as salmonella could be a more novel delivery vehicle. The DNA can also be coated on to microprojectiles and fired into the nuclei or target cells by a gene gun.

3.4 DNA Transfection

Many methods have been developed over the last 30 years to facilitate the introduction of DNA into cells which have greatly assisted, inter alia, our understanding of the control of gene expression.

Conventional methods to introduce DNA into cells are well known in the art and typically involve the use of chemical reagents, cationic lipids or physical methods. Chemical methods which facilitate the uptake of DNA by cells include the use of DEAE-Dextran (Vaheri and Pagano Science 175: p434). DEAE-dextran is a negatively charged cation which associates and introduces the DNA into cells but which can result in loss of cell viability. Calcium phosphate is also a commonly used chemical agent which when co-precipitated with DNA introduces the DNA into cells (Graham et al Virology (1973) 52: p456).

The use of cationic lipids (eg liposomes (Felgner (1987) Proc. Natl. Acad. Sci USA, 84:p7413) has become a common method since it does not have the degree of toxicity shown by the above described chemical methods. The cationic head of the lipid associates with the negatively charged nucleic acid backbone of the DNA to be introduced. The lipid/DNA complex associates with the cell membrane and fuses with the cell to introduce the associated DNA into the cell. Liposome mediated DNA transfer has several advantages over existing methods. For example, cells which are recalcitrant to traditional chemical methods are more easily transfected using liposome mediated transfer.

More recently still, physical methods to introduce DNA have become effective means to reproducibly transfect cells. Direct microinjection is one such method which can deliver DNA directly to the nucleus of a cell (Capecchi (1980) Cell, 22:p479). This allows the analysis of single cell transfectants. So called "biolistic" methods physically shoot DNA into cells and/or organelles using a particle gun (Neumann (1982) EMBO J, 1: p841). Electroporation is arguably the most popular method to transfect DNA. The method involves the use of a high voltage electrical charge to momentarily permeabilise cell membranes making them permeable to macromolecular complexes. However physical methods to introduce DNA do result in considerable loss of cell viability due to intracellular damage. These methods therefore require extensive optimisation and also require expensive equipment.

What is apparent from the above is that transfection of cells, either transiently or stably is a routine procedure undertaken by the man skilled in the art and is extensively referenced in academic publications, laboratory manuals and reference books. We have used both transient and stably transfected cell-lines to analyse the use of acetaminophen in GDEPT.

4. STATEMENT OF INVENTION

It is an object of the invention to provide a cancer therapy which reduces undesirable side effects of conventional cancer treatments.

It is a further object of the invention to provide a gene therapy based cancer treatment which targets cancer cells.

According to a first aspect of the invention there is provided a cancer therapy comprising:

i) administering to a mammal an effective amount of at least one vector capable of transfecting at least one tumour cell characterised in that said vector includes at least one P450 gene, or an effective part thereof, the expression of which is controlled by a promoter sequence, or the effective part thereof, which shows substantially tumour cell specific expression; and ii) administering a therapeutically effective amount of at least acetaminophen, or a structurally related derivative thereof.

In a preferred method of the invention said mammal is human.

In a further preferred method of the invention said vector is an expression vector conventionally adapted for eukaryotic expression.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites (eg glucose, lipids) or enviromental effectors (eg light, heat,).

Promoter elements also include so called TATA box and RNA polymerase initiation site (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic cell.

In addition adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction. Please see, Sambrook et al (1989) Molecular Cloning: A Laboratory Manual, Cold Spring Harbour Laboratory, Cold Spring Harbour, NY and references therein; Marston, F (1987) DNA Cloning Techniques: A Practical Approach Vol III IRL Press, Oxford UK.

In yet a further preferred method of the invention said vector is a viral based vector. Ideally said viral vector is selected from the following: adenovirus; retrovirus; adeno associated virus; herpesvirus; lentivirus; baculovirus.

Viral based vectors according to the invention may also include hybrid viral vectors which include advatageous features of selected viruses which facilitate, for example and not by way of limitation, viral infectivity, replication or expression of genes carried by said hybrid vector.

In a still further preferred method of the invention said promoter sequence is preferably selected from at least one of the following: TRP-1; HER2; HER3; ERBB2; ERBB3; CEA; MUC-1; α-fetoprotein; Rous sarcoma virus long terminal repeat; cytomegalovirus promoter; murine leukaemia long terminal repeat; simian virus 40 early and late promoters; herpes simplex virus thymidine kinase promoter; prostate specific antigen promoter (PSA); zilin gene promoter; pancreatic amylase promoter; tyrosinase related peptide promoter; tumour rejection antigen precursor promoters.

In yet a further preferred method of the invention said P450 gene is of mammalian origin; ideally human. More ideally still said P450 gene is human CYP1A2. Alternatively said P450 gene is either human CYP2E1 or CYP3A4.

In yet still a further preferred method of the invention said P450 is of non-human origin. Ideally said P450 gene is derived from a rodent. More ideally still said rodent P450 gene is selected from homologous rodent genes encoding CYP1A2; CYP2E1; or CYP3A4.

GDEPT which uses rodent homologues of P450 are advantageous since inhibitors of human CYP1A2, for example, furaphylline, can be used in conjunction with acetaminophen. As noted previously, the rodent homologue of CYP1A2, is resistant to this inhibitor than the human form of the enzyme. This would therefore enable the use of elevated levels of acetaminophen since toxic amounts of NABQI would not be generated in the liver.

The administration of the vector according to the invention to the mammal is by conventional techniques. Typically this includes, by example and not by way of limitation, intravenous, intramuscular or intraperitoneal injection; or direct injection into the tumour tissue.

In yet a still further preferred method of the invention said tumour cell is selected from at least one on the following cancers: breast; pancreatic; ovarian; cervical; lung; hepatic; retinal; renal; testicular; prostate; gastointestinal; glioma; melanoma; bladder; lymphoma; leukaemia; epithelial; mesothelial;

In yet still a further preferred method of the invention there is provided the use of acetaminophen in the manufacture of a medicament for the treatment of cancer.

According to a further aspect of the invention there is provided a cancer therapy comprising:
i) administering to a mammal an effective amount of at least one vector, capable of transfecting at least one tumour cell, characterised in that said vector includes at least one P450 gene, or an effective part thereof, the expression of which is controlled by a promoter sequence, or the effective part thereof, which shows substantially tumour cell specific expression;
ii) administering an effective amount of at least one agent capable of modulating the amount of glutathione in said mammal; and
iii) administering a therapeutically effective amount of acetaminophen, or a structurally related derivative thereof.

Agents capable of increasing glutathione in the liver are well known in the art and include, by example and not by way of limitation, methionine, acetylcysteine.

An embodiment of the invention will now be described, by example only, and with reference to the following Table and Figures;

Table 1 represents the bystander effect on viability produced by incubating H1A2 MZ cells (stably transfected with human CYP1A2) with various cell-lines in the presence of acetaminophen. Tumour cells or V79 MZ cells (non transfected, parental cells) were co-cultured overnight with various mixtures of H1A2 MZ cells (as indicated in the Table), washed with PBS and incubated with 4 mM acetaminophen in PBS for 6 h at 37° C. the cells were then washed once with PBS and maintained for either 24 or 48 h in culture medium appropriate to each cell type, as detailed in the Methods section. At 0, 6, 24 or 48 h the cells were washed in PBS and viability of the mixed cell population determined by trypan blue exclusion. The data shown are mean values±SEM of 4 separate determinations. Statistical significance was determined at each time point by comparing viability measurements in the mixed cell populations with both the viability determined at 0 h and in the absence of H1A2 MZ cells in the mixture 2×2 contingency tables using the 2-tailed Chi-squared test with Yate's correction. Viability was determined in a total of 1500 cells at each time point. Levels of significance are indicated as p<0.001; *p<0.0001;

Figure 3:
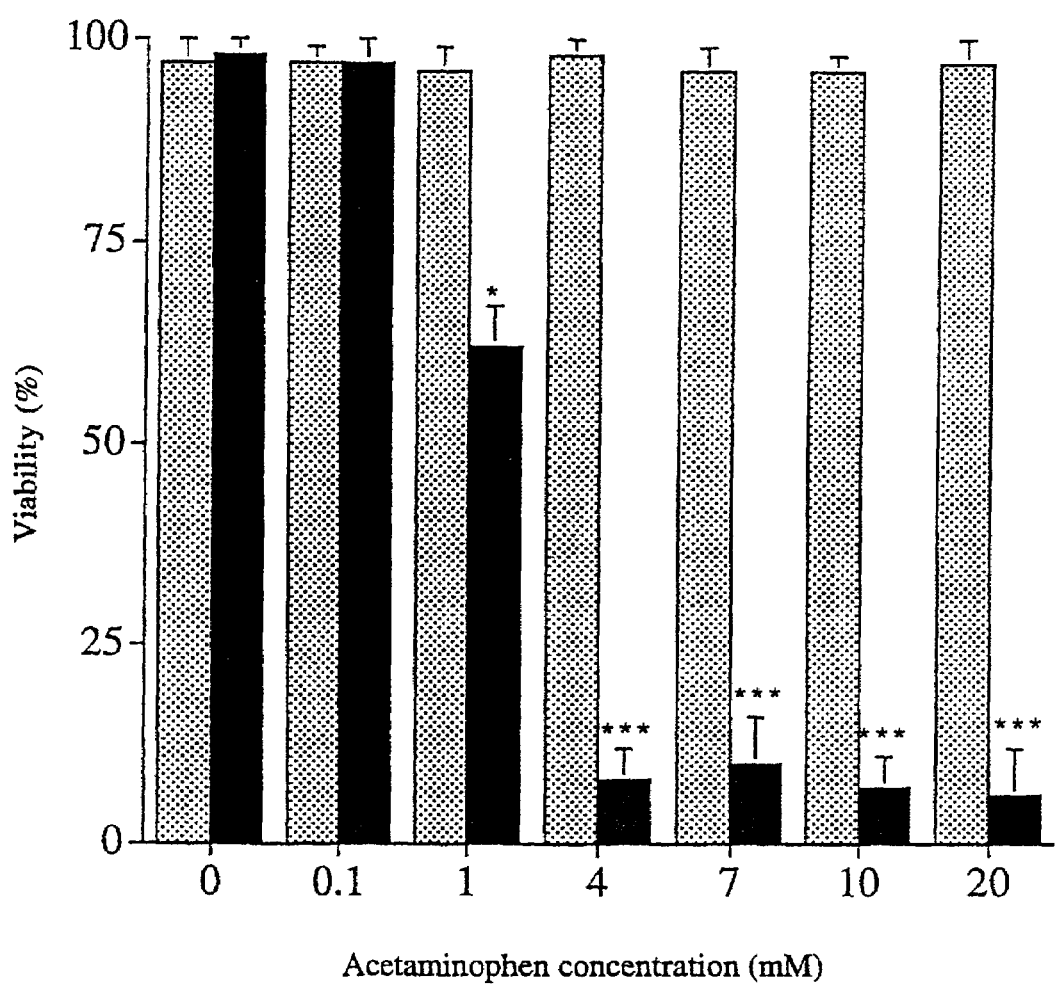
Figure 4:
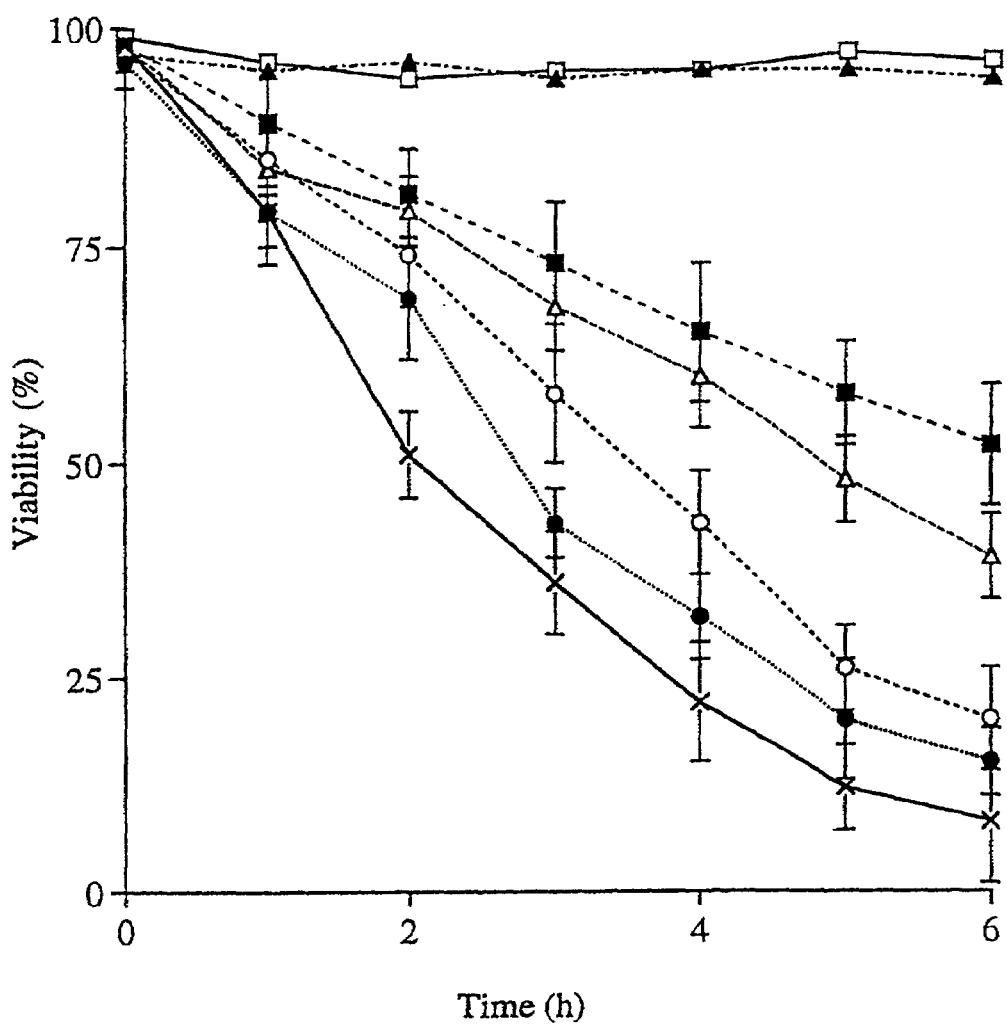

Acetaminophen concentration is 10 mM. Cell viability is monitored by tritiated thymidine incorporation;

FIG. 3 represents the effect of acetaminophen on the viability of stably transfected V79 MZ and H1A2 MZ cells. V79 MZ cells (stippled bars) and H1A2 MZ cells (filled bars) were allowed to adhere to the wells of tissue culture plates overnight, washed with PBS and then incubated with various concentrations of acetaminophen for 6 h at 37° C. Viability was determined by the ability of cells to exclude trypan blue. Data is represented as the mean±SEM of 4 separate determinations and analysed by comparing the viability in H1A2 MZ cells with V79 MZ cells at each concentration of acetaminophen using the 2-tailed unpaired Student's t-test. Levels of significance are indicated as *p<0.01; ***p<0.0001;

FIG. 4 represents the bystander effect on viability produced by incubating stably transfected, acetaminophen-activating H1A2 MZ cells with non-transfected parental V79 MZ cells. V79 MZ cells were co-cultured overnight with various mixtures of H1A2 MZ cells, washed with PBS and then incubated with 4 mM acetaminophen for up to 6 h at 37° C. The cells were then washed in PBS and the viability of the mixed cell population determined by trypan blue exclusion. The cultures comprised V79 MZ cells only (open squares), and V79 MZ cells mixed with 5% (solid squares), 10% (open triangles), 25% (open circles) and 50% (solid circles) H1A2 MZ cells. In addition, the viability of H1A2 MZ cells in the presence (crosses) and absence (solid triangles) of acetaminophen is shown. Data is represented as the mean±SEM of 4 separate determinations. Statistical analysis of the data at the 6 h time point is presented in Table 1.

Figure 5:
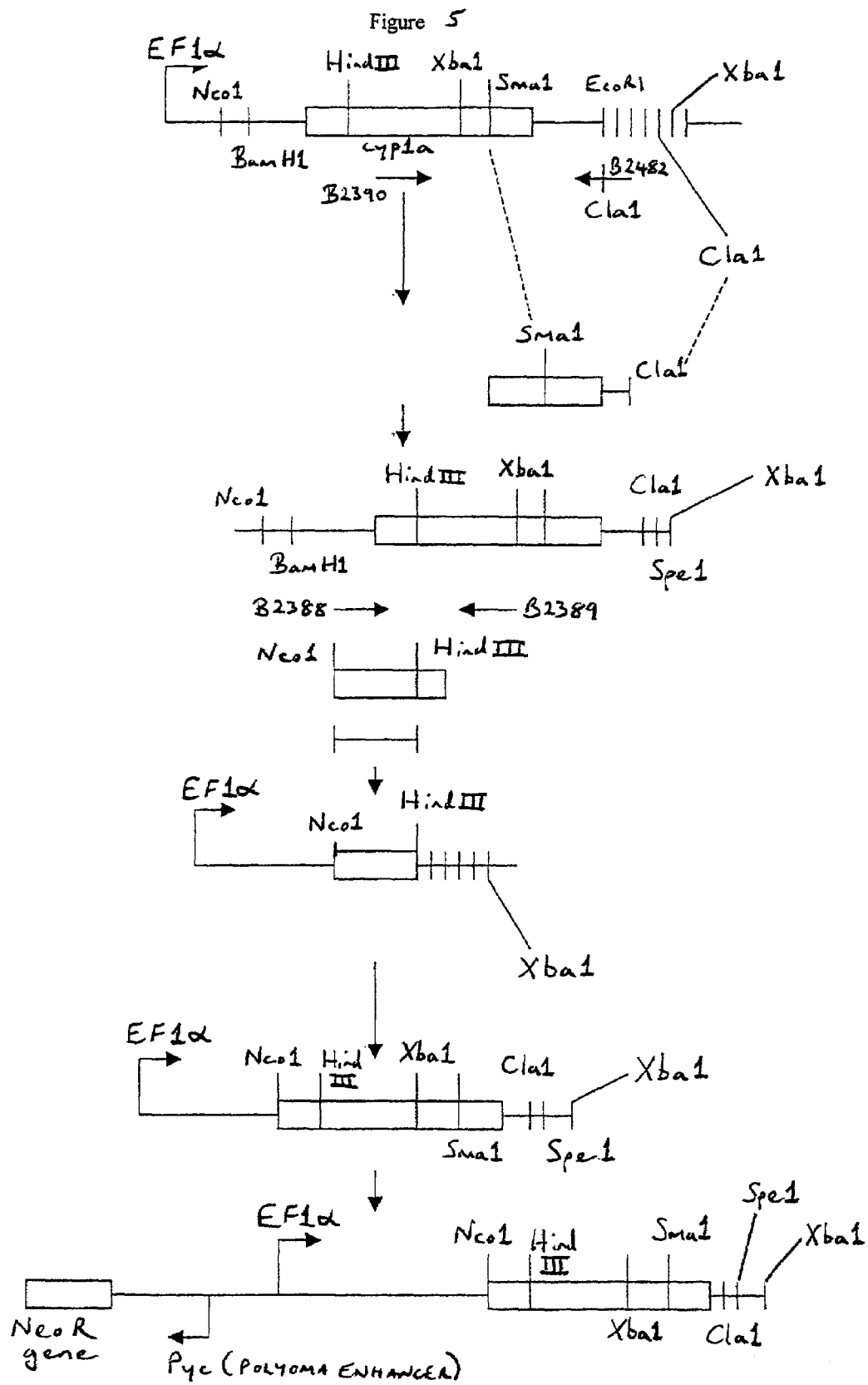

FIG. 5 represents the sub-cloning procedure to create the expression vector used in the transient transfection experiments; and FIG. 6 is the sequence of the vector pEFPlink 6 (SEQ ID NO:1).

5. MATERIALS AND METHODS

5.1.1. Recombinant DNA Techniques

The CYP1A2 cDNA is cloned downstream of a 544 bp fragment of the proximal 5' flanking region of the human ERBB2 gene in pBluescript II SK+ and then the chimeric minigene (ERBB2 promoter-CYP1A2 cDNA) is subcloned into a variety of eukaryotic expression vectors including:—

(a) the plasmid pPolyA (based on the commercial vector pcDNA [InVitrogen] from which the CMV promoter has been excised). Transfection is performed by application of plasmid DNA in the presence of cationic liposome complexes, either commercially obtained reagents such as Lipofectin (Life Technologies) or novel experimental agents (Genzyme). In order to allow for selection of genetically transformed clones the ERBB2-CYP1A2 plasmid is cotransfected at a 9:1 molar ratio with pSV2neo which encodes resistance to geneticin.

(b) the double copy retrovirus N2A, which allows conditional expression of the insert outside the transcription unit driven by the retroviral long terminal repeat promoter. Amphotropic retroviral stock is produced by packaging of the virus in GP +env AM12 cells.

(c) the adeno-associated virus vector psub 201, which when cotransfected into adenovirus-expressing cells together with pAAV/Ad leads to production of recombinant AAV that allows conditional expression of the insert in target cells.

The target cells in this example are human breast and pancreatic cancer cell lines which either over-express ERBB2 due to transcriptional upregulation or express normal (undetectable) levels.

5.1.2 Vector Construction for Transient Cell Transfection

A summary of the sub-cloning procedure is set-out in FIG. 5. Briefly, the following steps were undertaken. CYP1A2 was subcloned from pCR™Bac (Invitrogen) by digestion with restriction enzymes EcoR1 and BamH1. This fragment was sub-cloned into EcoR1/BamH1 digested pEFPlink.6 which is derived from pEFPlink2 (Marais et al (1995) EMBO J 14: 3136–3145). pEFPlinlk.6 is altered by the selective removal of restriction sites and the provision of a more versatile multiple cloning site. The sequence of pEF-Plink6 is given in FIG. 4.

The sub-cloned CYP1A2 gene was sequenced to confirm its identity to the published CYP1A2 sequence. The vector containing the CYP1A2 gene is/called pEF+cyp+.

Non-coding 5' and 3' sequences were then removed to generate restriction sites which facilitate the sub-cloning of CYP1A2 into a eukaryotic expresssion vector. CYP1A2 was PCR amplified and cut with Cla1 and Sma 1 and sub-cloned back into pEF+cyp+ to replace the original CYP1A2 gene. This removes much of the 3' untranslated region of the. This vector is called pEF+cyp. The 5' leader sequence was deleted in the following way. Sequence specific primers were used to to amplify CYP1A2 from pEF+Plink+ and create a Nco1 site. It is preferable to use the ATG initiation codon in the Nco1 site to ensure efficient translation initiation of CYP1A2. The amplified fragment was cut with Nco 1 and HindIII and subcloned into pEFPlink6. This vector was sequenced to confirm the sub-cloning. pEFPlink was cut with Nco1 and HindIII and subcloned into pEF+cyp. This vector was called pEFcyp1A2.

This modified CYPA 12 cDNA was then subcloned into the eukaryotic expression vector pMCEF which is derived from pEFPlink2 and contains the NeoR gene allowing selection in G418. The expression of the modified CYP1A2 cDNA is under the control of the elongation factor 1α promoter, (Marais et al Cancer Research (1996) 56: 4735–42). This was done by digestion of pEFcypA2 with Nco1 and Spe 1 and sub-cloning the fragment containing the modified CYP1A2 into pMCEF to generate the expression vector pMCEFcyp1A2.

pMCEFcyp1A2 incorporating mouse CYP1A2 was used in transient transfection experiments described below.

5.2 Transient Cell Transfection Using LipofectAMINE

LipofectAMINE (LPA)(Gibco BRL UK) is a lipid reagent that transfers DNA into cells and has proven to be very successful for transiently transfecting cells. We have found that we can achieve transfection frequencies approaching 50% (depending on cell-line and DNA construct). This compares very favourably with DEAE-dextran transfection which can only achieve approximately 0.5–2.5% efficiency. We estimate that LPA only results in 5% cell death when compared to 50% cell death when using DEAE-dextran.

COS cells are plated at $1.5 \times 10^5$ per well in 6 well tissue culture dishes the evening before transfection. Cells are left to grow overnight in Dulbecco-Vogt's Modified Eagles Medium (DMEM) supplemented with 10% foetal calf serum, 2 mM L-glutamine, penicillin (100 U/ml) and streptomycin (100 µg/ml). All tissue culture reagents can be obtained from Gibco BRL, Paisley, UK.

LPA/DNA complexes are prepared in accordance with the manufactures instructions. Briefly the following steps are undertaken. On the day of the transfection experiment dilutions of vector DNA are prepared in PBSA (0.4 g KCl, 8.0 g NaCl, 0.2 g $KH_2PO_4$, 1.15 g $Na_2HPO_4$ per liter) containing 0.5% (w/v) albumin. It is important not to use polypropylene reaction tubes as the LPA/DNA complex will adhere to the plastic.

Vector DNA is prepared at 0.4–0.6 µg per transfection in 16 µl of PBSA. Typically a stock of vector DNA is prepared at 0.025 µg/ml in PBSA for use in transfection experiments. In experiments were more than one vector is used the same concentration of DNA is to be used and the volume adjusted accordingly. Note that when using multiple vectors it is important to mix the vectors prior to addition of LPA.

Typically, when preparing the LPA/DNA complex squares approximatelly 1 cm×1 cm are marked onto the bottom of a petri dish corresponding to the number of transfection to be conducted. 10–12 µl PBSA is placed into the centre of each marked square to which 4–6 µl of LPA is added to give a total volume of 14–16 µl. To this reaction mix is added 16 µl stock vector DNA and the LPA/DNA complex is thoroughly mixed by passage through a micropipette tip by sucking the reaction mixture up and down 6–8 times. The reaction mixture is then left in the covered petri dish for approximtely 15 minutes.

During this incubation period, cells to be transfected are washed with serum free medium and then 800 µl of serum free medium added prior to adddition of the complexed LPA/DNA.

To the LPA/DNA complex, 200 µl of serum free medium is added to each LPA/DNA sample which is then gently added to the cells over a period of 3–4 seconds. Cells are returned to a 37° C. $CO_2$ incubator for 6 hours. Cells are washed twice in medium and 2.5 ml of fresh medium is added to the cultures. Cultures can then be assayed at any time to monitor transgene expression.

The above described method provides reliable, high level expression of transgenes carried by vector DNA. The method is readily undertaken by the man skilled in the art.

5.3 Western Blotting

The level of expression of CYP1A2 is measured by Western blot analysis utilizing anti-peptide antibodies described in the literature (Edwards R J et al, Biochem Pharmacol 1993; 46: 213–220 and Murray B P et al, Carcinogenesis 1993; 14: 585–592). These antibodies bind specifically to CYP1A2 in human liver microsomal fraction. In addition, one of the antibodies has been shown to bind readily to CYP 1A2 expressed in a human B lymphoblastoid cell line transfected with a plasmid vector expressing human CYP1A2. In these cells the level of expression of human CYP1A2 was similar to that found in human liver, ie 8 pmols per mg protein (Edwards R J et al, Carcinogenesis 1994; 15: 829–836). Microsomal fractions are prepared from tumour cells transfected with human CYP1A2, or cells transfected with an unrelated gene, eg cytosine deaminase, in the same vectors. Washed cells are disrupted using a Dounce homogeniser and the microsomal fraction prepared by ultracentrifugation and stored frozen at −80° C. as described previously. Western blotting of microsomal fractions is performed as described previously (Boobis A R et al, Br J Clin Pharmacol 1980; 9: 11–19) employing enhanced chemiluminescence to maximise sensitivity.

5.4 Biochemical Activity of CYP1A2

In addition, the functional activity of expressed human CYP1A2 is determined in the tumour cells by measuring the rate of O-deethylation of phenacetin. At an appropriate substrate concentration (4 µM) this reaction is specifically catalysed by CYP1A2 in human liver microsomal fraction. Tumour cell microsomal fractions prepared as described above are incubated at 37° C. in the presence of NADPH and the production of acetaminophen is determined by gas chromatography/negative ion chemical ionisation mass spectrometry using deuterated acetaminophen as internal standard. This highly sensitive assay easily measures CYP1A2 activity in small quantities (<10 µg) of human liver microsomal fraction which typically has an activity of 70 pmols/min/mg protein.

5.5 Cell Viability

Two methods were employed to monitor cell viability; exclusion of trypan blue by viable cells followed by cell counting; and incorporation of tritiated thymidine as a measure of DNA synthesis.

5.5.1 Trypan Blue Exclusion

For cell viability experiments 200,000 cells per well were plated on 12 well plates (Beckton-Dickenson, Oxford, UK), using the medium and conditions required by the tumour cell line and allowed to adhere overnight. After this the cells were washed with PBS before the addition of acetaminophen in 0.1 ml PBS (concentrations of 0.1–20 mM acetaminophen were dissolved in PBS by sonication) and then maintained at 37° C. At the appropriate time points, cells were removed from the plates by trypsinisation and collected by centrifugation. Cell viability was measured as ability to exclude trypan blue. Cells were counted at ×100 magnification using an Improved Neubauer haemocytometer; all cell counts are the mean of duplicate determinations of five fields from duplicate experiments.

5.5.2 $^3$H-Thymidine Incorporation as a Measure of Cell Division

Transfected COS cells are either exposed to various concentrations of acetaminophen or incubated in the presence of 10 mM acetaminophen and cell viability monitored with time. $^3$H-thymidine (Amersham International UK, 100 Ci/mmol, 5 µCi per assay), is added to treated and control cultures and aliquots removed and acid precipitable counts assessed by liquid scintillation using a Beckton Liquid Scintillation Counter.

5.6 Glutathione Depletion.

The intracellular glutathione content, comprising reduced and oxidised forms of glutathione is measured using a kinetic assay in which glutathione in the presence of glutathione reductase catalyses the continuous reduction of 5,5'-dithio-bis(2-nitrobenzoic acid) by NADPH. The rate of the reaction is proportional to the concentration of glutathione. The reaction is monitored at 412 nm and quantified by comparison with standards.

5.7 Measurement of [$^{14}$C] Acetaminophen

Covalent binding of radioactivity to cell protein following exposure to radioactive acetaminophen. Cells are incubated for up to 90 min with [$^{14}$C]acetaminophen. After washing, cellular protein is precipitated with trichloroacetic acid and the precipitate washed extensively with 80% methanol to remove unbound radioactivity. The protein pellet is digested in sodium hydroxide, neutralised, and the bound radioactivity measured by scintillation spectroscopy.

5.9 Cell Culture of Stably Transfected Cell-Lines

V79 MZ Chinese hamster cells were maintained in Dulbecco-Vogt's modified Eagle's Medium (DMEM) supplemented with 10% foetal calf serum 9FCS), 2 mM L-glutamine, penicillin (100 U/ml and streptomycin (100 μg/ml) (all tissue culture reagents were obtained from Gibco BRL, Paisley, UK). H1A2 MZ cells, which are V79 MZ cells transfected with the human CYP1A2 gene, were also maintained in supplemented DMEM with the addition of geneticin at a concentration of 4 mg/ml. SK-OV-3 cells were grown in DMEM supplemented with 15% FCS and 2 mM L-glutamine, without the addition of antibiotics. RPMI-1640 medium with 10% FCS, 2 mM L-glutamine, penicillin (100 U/ml) and streptomycin (100 pg/ml) was required by the HCT116 cells. These cell lines were maintained at 37° C. with 100% humidity and 5% $CO_2$. MDA-MB-361 cells were grown in Leibovitz (L-15) medium supplemented with 15% FCS and 2 mM L-glutamine maintained at 37° C. with 100% humidity and did not require $CO_2$. At confluence cells were removed from tissue culture flasks by inubation with trypsin-EDTA for 5 min, diluted 1:3–1:6 in fresh medium and seeded onto fresh flasks. The tumour cell lines were obtained from the European Collection of Cell Cultures.

5.9. Stably Transfected H1A2 MZ Cells

The expression of human CYP1A2 in these cells was confirmed by measurement of 7-ethoxyresorufin O-deethylase and 7-methoxyresorufin O-deethylase activities on a cytosol-free protein fraction as described previously.[9] The respective values obtained of 5.4±0.1 and 12.1±0.2 pmol/min/mg protein (n=6) are/similar to those reported previously, i.e. 6.5 and 12.8 pmol/min/mg protein[9] and n6 activity was detected in the parental V79 MZ cells. Further, the expression of human CYP1A2 in the cytosol-free protein fraction of H1A2 MZ cells, but not V79 MZ cells was also demonstrated by western blotting using an antibody specific for this P450 enzyme[10] (data not shown).

6. RESULTS

We show that transient transfection of COS cells using LPA with a vector carrying CYP1A2 under the control of a promoter which shows enhanced expression in tumour cells is capable of sensitising cells to therapeutically relevant concentrations of acetaminophen.

Figure 1:
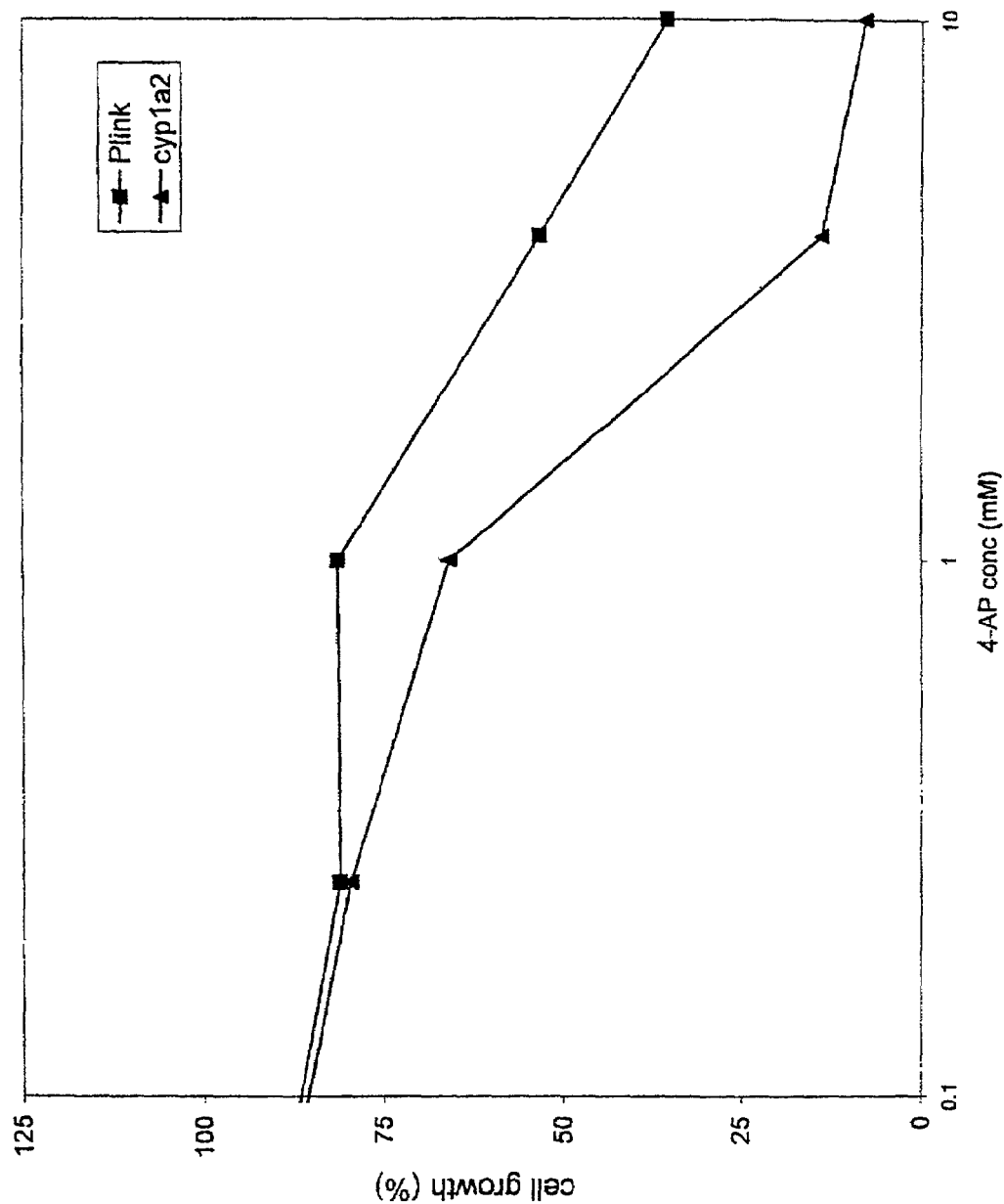
FIG. 1 is a graphical representation of an acetaminophen titration showing the sensitivity of COS cells transiently transfected with a vector incorporating mouse CYP1A2 and non-transfected control COS cells. Cell viability is monitored by tritiated thymidine incorporation.

FIG. 1 shows an acetaminophen titration comparing transfected COS cells with non-transfected control COS cells. Cells were transfected and allowed to recover and express CYP1A2 for 48 hrs. Although non-transfected parental cell-lines show some sensitivity to acetaminphen, as measured by tritiated thymidine incorporation, transfected cells show a significant increase in sensitivity. The apparent sensitivity of control cells to acetaminophen can be attributed to the fact that COS cells contain a significant amount of p450 activity which will result in the production of NABQI in the presence of acetaminophen. However by increasing the basal levels of p450, by transfection with CYP1A2 it is shown that the administration of less acetaminophen results in reduced cell viability for an equivalent amount of acetaminophen, please see FIG. 1, 4 mM acetaminophen concentration.

Figure 2:
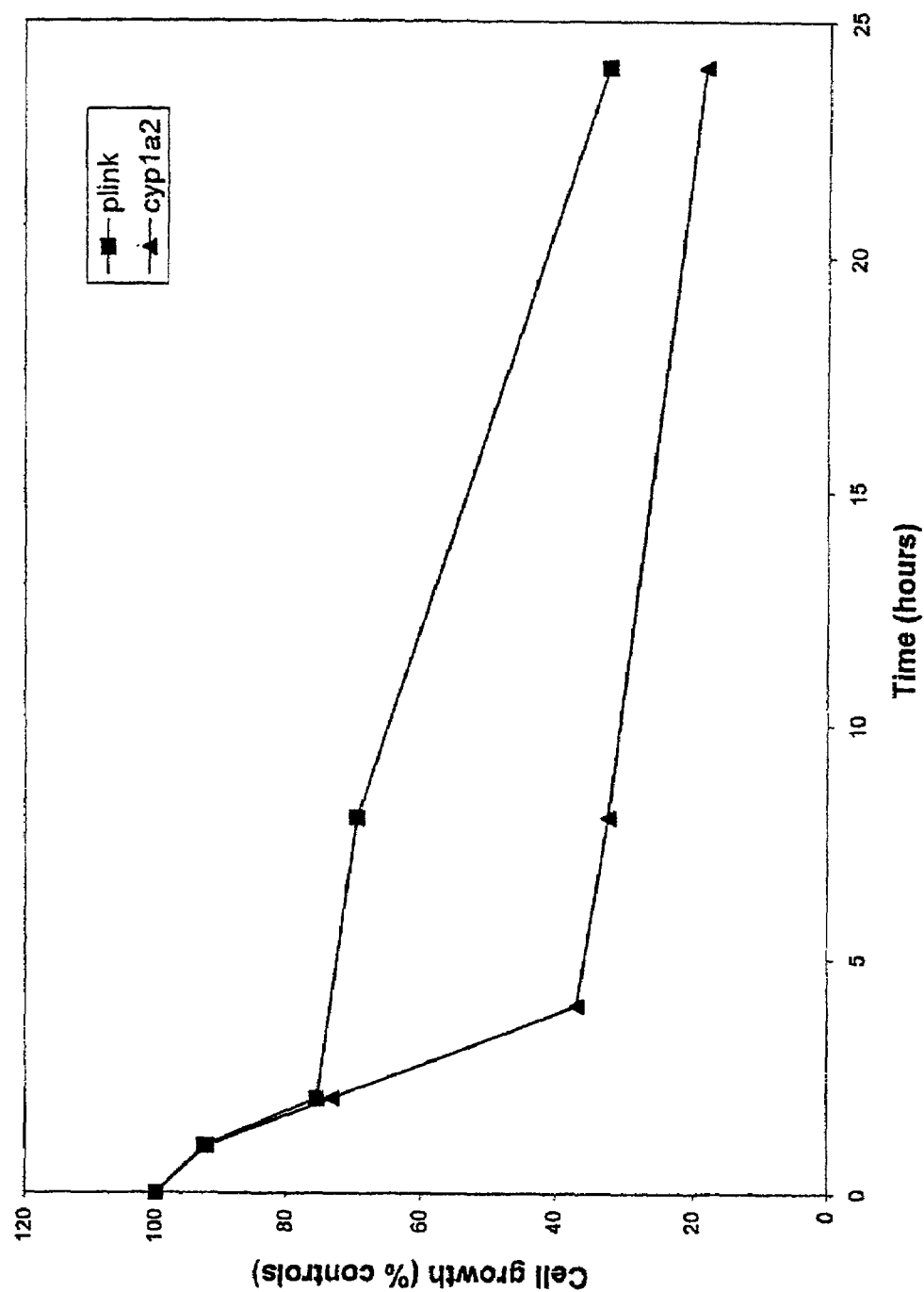
FIG. 2 is a cell viability time course of COS cells transiently transfected with mouse CYP1A2 and non-transfected control COS cells over a 24 hr period.

FIG. 2 shows a COS cell viability time course in response to 10 mM acetaminophen. COS cells were transfected and compared to non-transfected control cells over a period of 24 hrs. The extent of acetaminophen sensitivity increases markedly during the first 4–8 hrs. This correlates with the expression of CYP1A2 as monitored by western blot, results not shown. The sensitivity of transiently transfected COS cells is likely to be an underestimate of what may be achieved in stable cell-lines expressing CYP1A2 or in vivo in transgenic animal models since the vector DNA is susceptible to nuclease digestion resulting in a gradual decrease in potential sensitivity. This is, of course, is not shown by the control cells since the reduction in cell viability is the result of endogenous expression of p450 which is ongoing.

These results indicate that transiently transfected COS cells can be sensitised to acetaminophen by expression of a vector carrying a gene encoding CYP1A2. These results are confirmed by producing cell lines stably transfected with CYP1A2 which is described below.

Incubating H1A2 MZ cells, which stably express CYP1A2, with a range of concentrations of acetaminophen (0.1–20 mM) for 6 h allowed the determination of cytotoxic concentrations (FIG. 1). No cytotoxicity was observed in the absence of acetaminophen or with 0.1 mM acetaminophen. However, after exposure to 1 mM acetaminophen viability fell to 62%. Incubation with 4 mM acetaminophen resulted in a further reduction in viability to 8%. Higher concentrations of acetaminophen resulted in a similar amount of cell killing, FIG. 3. In contrast, incubation of V79 MZ cells, which lack CYP1A2, with acetaminophen resulted in no loss of cell viability, FIG. 3. Therefore, as 4 mM acetaminophen was the minimum dose to give the maximum effect, this concentration was selected for further experiments.

To determine if the toxic metabolite produced by CYP1A2 had a cytotoxic effect on bystander cells incapable of activating acetaminophen, H1A2 MZ cells were mixed with V79 MZ cells before exposure to 4 mM acetaminophen. The percentage decline in total cell viability greatly exceeded the percentage of acetaminophen-activating cells in the mixture indicating a significant bystander effect, FIG. 4. In the presence of 5% H1A2 MZ cells the viability of the mixed cell population was reduced to 52%, and as the proportion of H1A2 MZ cells was increased the number of viable cells in the mixture declined (FIG. 4, Table 1) and a near maximal effect was found with a mixture of an equal number of V79 MZ and H1A2 MZ cells, FIG. 4. In contrast, no decline in cell viability was observed in V79 MZ cells incubated in 4 mM acetaminophen or H1A2 MZ cells incubated in phosphate-buffer saline (PBS) without acetaminophen (FIG. 4, Table 1).

The susceptibility of tumour-derived cells to cytotoxicity produced by the activation of acetaminophen was investigated by mixing H1A2 MZ cells with SK-OV-3, HCT116 and MDA-MB-361 cells and incubating them in the presence of 4 mM acetaminophen for 6 h. It was found that like V79 MZ cells, SK-OV-3 cells were highly sensitive as viability fell progressively as the prorportion of H1A2 MZ cells was increased (Table 1). HCT116 cells showed a disproportionate decrease in viability when incubated with 5 and 10% H1A2 MZ cells, although with 50% H1A2 MZ cells the amount of cell killing could be accounted for by loss of H1A2 MZ cells alone (Table 1). However, MDA-MB-361 cells appeared to be highly resistant to cytotoxicity as the reduction in cell viability was similar to the proportion of H1A2 MZ cells present (Table 1).

To determine if the residual viable cells were programmed to die, as we have found previously,[11] attempts were made to culture the various cell types in normal growth medium after they had been exposed to acetaminophen for 6 h in the presence of the activating H1A2 MZ cells. It was found that after 24 h in culture, the viability of V79 MZ, SK-OV-3 and HCT116 cells mixed with as little as 5% H1A2 MZ cells fell to zero (Table 1). Only MDA-MB-361 cells showed resistance to cell killing, although even with these cells viability was reduced to 18% in cultures comprising an equal number of MDA-MB-361 and H1A2 MZ cells and no viable cells were found after 48 h (Table 1). Nevertheless, with fewer H1A2 MZ cells present viability increased with time, presumably as the number of dividing MDA-MB-361 cells increased during culture.

7. DISCUSSION

Acetaminophen can be activated by oxidation catalysed by human CYP1A2 to form the cytotoxic compound NABQI. The combination of acetaminophen as prodrug and CYP1A2 as activating enzyme has a potential application in GDEPT. It has been demonstrated here that a sufficient amount of NABQI produced in cells transfected with human CYP1A2 to cause cyotoxicity. Further, enough NABQI is released from activating cells to cause cytotoxicity in neighbouring cells. Such a bystander effect was readily demonstrated in V79 MZ cells. However, human tumour-derived cells showed a range of sensitivities. An extensive bystander effect was found using SK-OV-3 cells, an ovarian tumour derived cell line, whereas, HCT-116 cells, which are derived from a colon tumour, appeared to be somewhat more resistant to the cytotoxic effect of NABQI when assessed immediately after a 6 h incubation period. However, both of these tumour cell types appeared to have been markedly damaged by exposure to NABQI as they failed to survive in culture. On the other hand, the MDA-MB-361 cells, which originate from a breast tumour, displayed resistance of the cytotoxic effect of NABQI, with only those cells exposed to the highest concentration being affected.

NABQI is capable of arylating and oxidising protein thiol groups, although studies with thiol reductants such as dithiothreitol[11] and N-acetylcysteine[12] suggested that the reversible oxidation of thiols (i.e. "oxidative stress") rather than arylation is responsible for cell death from acetaminophen.[6] Irrespective of the exact mechanism, the key factors that determine the toxicity of acetaminophen are the rate of production of NABQI as determined by the activity of the relevant cytochrome P450 enzymes and the starting level and extent of depletion of GSH. Thus rat liver is relatively resistant to acetaminophen, but not pre-formed NABQI, because the rate of formation of the reactive metabolite is insufficient, even at very high concentrations of acetaminophen, to deplete GSH. In contrast, hamsters are very sensitive because acetaminophen is rapidly and extensively oxidised to NABQI. Human liver hepatocytes exhibit a range of sensitivities which correlate with the rate of oxidation of acetaminophen to NABQI.[13] Toxicity in overdosed individuals is confined to the liver which is the only organ that has the required level of enzyme activity to generate NABQI to deplete GSH, a prerequisite for cell damage and death. The hepato-toxicity of acetaminophen can be greatly increased in all species by prior depletion of GSH with chemicals such as diethylmaleate.[14] Thus the toxicity of acetaminophen is dependent upon the balance between the activity of the NABQI-generating enzyme and the concentration of GSH.

GSH concentrations in breast tumours (913 nmol/g tissue) are two-fold greater than in normal breast tissue[15] but are less than 20% of those found in normal human liver (>5000 nmol/g tissue). Thus if tumour cells can be made to express NABQI-producing activity similar to human liver, therapeutic doses of acetaminophen should be selectively cytotoxic to the tumour cells. In addition, it will be possible to selectively protect the liver from any toxic effects of acetaminophen by oral administration of GSH precursors such as methionine or N-acetylcysteine[16] that elevate GSH in the liver but not other tissues.[17]

It might be possible to increase the efficiency of the enzyme activating system by replacing human CYP1A2 with another P450 enzyme with a greater capacity for acetaminophen activation. Although human CYP2E1 and CYP3A4 are known to catalyse this reaction,[7] the rates relative to CYP1A2 at high concentrations of acetaminophen have yet to be determined. Alternatively, the orthologous rodent forms of CYP1A2, CYP2E1 or CYP3A4 may provide the source of a more efficient enzyme.

REFERENCES

1. Connors T A. The choice of prodrugs for gene directed enzyme prodrug therapy of cancer. *Gene Ther.* 1995;2: 702–709
2. Harris J D, Gutierrez A A, Hurst H C, Sikora K, Lemoine N R. Gene therapy for cancer using tumour-specific prodrug activation. *Gene Ther.* 1994;1:170–175
3. Davidson D G, Eastham W N. Acute liver necrosis following overdose of acetaminophen. *Br Med J.* 1966; 5512:-1990.
4. Mitchell J R, Jollow D J, Potter W Z, Gillette J R, Brodie B B. Acetaminophen-induced hepatic necrosis. IV. Protective role of glutathione. *J Pharmacol Exp Ther.* 1973; 187: 211–217
5. Miner D J, Kissinger P T. Evidence for the involvement of N-acetyl-p-quinoneinine in acetaminophen metabolism. *Biochem Pharmacol.* 1979;28: 3285–3290.
6. Boobis A R, Fawthrop D J, Davies D S. Mechanisms of cell death. *Trents Pharmacol Sci.* 1989;10:275–280.
7. Patten C J, Thomas P E, Guy R L, Lee M, Gonzalez F J, Guengerich F P, Yang C S. Cytochrome P450 enzymes involved in acetaminophen activation by rat and human liver microsomes and their kinetics. *Chem Res Toxicol.* 1993;6:511–518.
8. Thatcher N J, Murray S, Edwards R J, Davies D S. Measurement of N-acetylbenzoquinoneimine formation by human hepatic microsomes. *12th International Symposium on microsomes and Drug Oxidations* 1998; abstract 74.
9. Wolfel C, Heinrich-Hirsch B, Schulz-Schalge T, Seidel A, et al. Genetically engineered V79 Chinese hamster cells for stable expression of human cytochrome P4501A2. *Eur J Pharmacol.* 1992;228:95–102
10. Edwards R J, Murray B P, Singleton A M, Murray S, Davies D S, Boobis A R. Identification of the epitope of an anti-peptide antibody which binds to CYP1A2 in many species including man. *Biochem Pharmacol* 1993;46: 213–220.

11. Tee L B, Boobis A R, Huggett A C, Davies D S, Reversal of acetaminophen toxicity in isolated hamster hepatocytes by dithiothreitol. *Toxicol Appi Pharmacol.* 1986;83:294–314.
12. Boobis A R, Tee L B, Hampden C E, Davies D S. Freshly isolated hepatocytes as a model for studying the toxicity of acetaminophen. *Food Chem Toxicol.* 1986;24:731–736.
13. Tee L B, Davies D S, Seddon C E, Boobis A R. Species differences in the hepatotoxicity of acetaminophen are due to differences in the rate of conversion to its cytotoxic metabolite. *Biochem Pharmacol.* 1987;36: 1041–1052.
14. Potter W Z, Thorgeirsson S S, Jollow D J, Mitchell J R. Acetaminophen-induced hepatic necrosis. V. Correlation of hepatic necrosis, covalent binding and glutathione depletion in hamsters. *Pharmacology.* 1974;12: 129–143.
15. Perry R R, Mazetta J A, Levin M, Barranco S C. Glutathione levels and variability in breast tumours and normal tissue. *Cancer.* 1993; 72: 783–787.
16. McLean A E, Day P A. The effect of diet on the toxicity of acetaminophen and the safety of acetaminophen-methionine mixtures. *Biochem Pharmacol.* 1975; 24: 37–42.
17. Aebi S, Lauterburg B H. Divergent effects of intravenous GSH and cysteine on renal and hepatic GSH. *Am J Physiol.* 1992; 263:348–352.

TABLE 1

| Cell type | H1A2 MZ cells (%) | Viability (%) | | | |
|---|---|---|---|---|---|
| | | 0 h | 6 h | 24 h | 48 h |
| V79 MZ | 0 | 99 ± 1 | 94 ± 7 | 98 ± 1 | — |
| | 5 | 98 ± 1 | 52 ± 5*** | 0 ± 0*** | — |
| | 10 | 98 ± 1 | 39 ± 6*** | 0 ± 0*** | — |

TABLE 1-continued

| Cell type | H1A2 MZ cells (%) | Viability (%) | | | |
|---|---|---|---|---|---|
| | | 0 h | 6 h | 24 h | 48 h |
| | 25 | 97 ± 2 | 20 ± 4*** | 0 ± 0*** | — |
| | 50 | 96 ± 3 | 15 ± 7*** | 0 ± 0*** | — |
| SK-OV-3 | 0 | 97 ± 1 | 98 ± 2 | 96 ± 3 | — |
| | 5 | 98 ± 1 | 55 ± 2*** | 0 ± 0*** | — |
| | 10 | 98 ± 1 | 43 ± 7*** | 0 ± 0*** | — |
| | 25 | 97 ± 1 | 22 ± 11*** | 0 ± 0*** | — |
| | 50 | 98 ± 1 | 16 ± 9*** | 0 ± 0*** | — |
| HCT116 | 0 | 96 ± 1 | 96 ± 5 | 96 ± 2 | — |
| | 5 | 98 ± 1 | 69 ± 9*** | 0 ± 0*** | — |
| | 10 | 98 ± 1 | 60 ± 6*** | 0 ± 0*** | — |
| | 25 | 97 ± 1 | 56 ± 4*** | 0 ± 0*** | — |
| | 50 | 98 ± 1 | 42 ± 6*** | 0 ± 0*** | — |
| MDA-MB-361 | 0 | 96 ± 1 | 98 ± 4 | 95 ± 3 | 97 ± 1 |
| | 5 | 98 ± 2 | 85 ± 2** | 84 ± 7** | 92 ± 4 |
| | 10 | 96 ± 3 | 74 ± 7*** | 81 ± 9** | 94 ± 7 |
| | 25 | 97 ± 1 | 70 ± 11*** | 78 ± 9*** | 91 ± 6 |
| | 50 | 98 ± 3 | 42 ± 4*** | 18 ± 5*** | 0 ± 0*** |

The invention claimed is:

1. A method for inhibiting the growth of cancerous cells in a mammal, the method comprising:
   i) administering directly to said cancerous cells a therapeutically effective amount of a vector comprising a promoter operably linked to a polynucleotide encoding a polypeptide selected from the group consisting of Cytochrome P450 1A2 (CYP1A2), Cytochrome P450 2E1 (CYP2E1), and Cytochrome P450 3A4 (CYP3A4), wherein said polypeptide is expressed in an efective amount to convert acetaminophen to a cytotoxic molecule, and
   ii) administering to the mammal a cancer-treating amount of acetaminophen,
   whereby the growth of the cancerous cells is inhibited.

2. The method according to claim 1, wherein said mammal is human.

3. The method according to claim 1, wherein said vector is a eukaryotic expression vector.

4. The method according to claim 1, wherein said vector is a viral vector.

5. The method according to claim 4, wherein said viral vector is a hybrid viral vector.

6. The method according to claim 4, wherein said viral vector is obtained from a virus selected from the group consisting of adenovirus, retrovirus, adeno-associated virus, herpes virus, lentivirus, and baculovirus.

7. The method according to claim 1, wherein said promoter is selected from the group consisting of N-(5'-phosphoribosyl)anthranilate isomerase (TRP-1) promoter, human epidermal growth factor receptor 2 (HER2/neu/c-erbB2 proto-oncogene or HER2) promoter, HER3 promoter, v-erb-b2 erythroblastic leukemia viral oncogene homolog 2 (ERBB2) promoter, ERBB3 promoter, carcinoembryonic antigen (CEA) promoter, Mucin 1 (MUC-1) promoter, α-fetoprotein promoter, Rous sarcoma virus long terminal repeat, cytomegalovirus promoter, murine leukemia long terminal repeat, simian virus 40 early and late promoters, herpes simplex virus thymidine kinase promoter, prostate specific antigen promoter (PSA), villin gene promoter, pancreatic amylase promoter, tyrosinase related peptide promoter, and tumor rejection antigen precursor promoter.

8. The method according to claim 1, wherein said promoter is a hybrid promoter.

9. The method according to claim 1, wherein said promoter is a tumor-specific promoter.

10. The method according to claim 9, wherein said tumor-specific promoter is selected from the group consisting of TRP-1, HER2, HER3, ERBB2, ERBB3, CEA, MUC1, α-fetoprotein, pancreatic amylase promoter, tyrosinase related peptide promoter, and tumor rejection antigen precursor promoter.

11. The method according to claim 1, wherein said promoter is a constitutive promoter.

12. The method according to claim 11, wherein said constitutive promoter is selected from the group consisting of villin gene promoter, Rous sarcoma virus long terminal repeat, cytomegalovirus promoter, murine leukemia long terminal repeat, simian virus 40 early and late promoters, and herpes simplex virus thymidine kinase promoter.

13. The method according to claim 1, wherein said polynucleotide is a mammalian polynucleotide.

14. The method according to claim 13, wherein said polynucleotide is a human polynucleotide.

15. The method according to claim 13, wherein said polynucleotide is a rodent polynucleotide.

16. The method according to claim 15, wherein the mammal is a human, and wherein the method further comprises administering to the mammal an effective amount of furaphylline that inhibits the activity of human CYP1A2, CYP2E1, or CYP3A4 in cells of the human.

17. The method according to claim 16, wherein the polypeptide is selected from the group consisting of rodent CYP1A2, rodent CYP2E1, and rodent CYP3A4.

18. The method according to claim 1, wherein the polypeptide is CYP1A2.

19. The method according to claim 1, wherein said cancer is selected from the group consisting of breast, pancreatic, ovarian, cervical, lung, hepatic, renal, testicular, prostate, gastrointestinal, glioma, melanoma, bladder, lymphoma, leukemia, epithelial, mesothelial, and retinal cancer.

20. The method of inhibiting the growth of cancerous cells in a mammal, the method comprising, concurrently or in sequence:
  i) administering directly to said cancerous cell an effective amount of at least one vector, wherein said vector comprises a promoter operably linked to a polynucleotide encoding a polypeptide selected from the group consisting of Cytochrome P450 1A2 (CYP1A2), Cytochrome P450 2E1 (CYP2E1), and Cytochrome P450 3A4 (CYP3A4), wherein said polypeptide is expressed in an effective amount to convert acetaminophen to a cytotoxic molecule;
  ii) administering to said mammal an effective amount of at least one agent selected from the group consisting of methionine and acetylcysteine; and
  iii) administering to said mammal an effective amount of acetaminophen,
  whereby the growth of the cancerous cells is inhibited.

21. The method of claim 20, wherein the vector, agent and acetaminophen are administered sequentially.

22. A composition of matter comprising acetaminophen; and a vector comprising a polynucleotide encoding a polypeptide selected from the group consisting of CYP1A2, CYP2E1, and CYP3A4 wherein the polypeptide converts acetaminophen to a cytotoxic molecule, and wherein the expression of the polynucleotide is controlled by a promoter.

23. The composition according to claim 22, wherein the vector is a eukaryotic expression vector.

24. The composition according to claim 22, wherein the vector is a viral vector.

25. The composition according to claim 24, wherein the viral vector is obtained from a virus selected from the group consisting of adenovirus, retrovirus, adeno-associated virus, herpesvirus, lentivirus, and baculovirus.

26. The composition according to claim 22, wherein the vector is a hybrid viral vector.

27. The composition according to claim 22, wherein said promoter is selected from the group consisting of TRP-1 promoter, HER2 promoter, HER3 promoter, ERBB2 promoter, ERBB3 promoter, CEA promoter, MUC1 promoter, α-fetoprotein promoter, Rous sarcoma virus long terminal repeat, cytomegalovirus promoter, murine leukemia long terminal repeat, simian virus 40 early and late promoters, herpes simplex virus thymidine kinase promoter, prostate specific antigen promoter (PSA), villin gene promoter, pancreatic amylase promoter, tyrosinase related peptide promoter, and tumor rejection antigen precursor promoter.

28. The composition according to claim 22, wherein said promoter is a hybrid promoter.

29. The composition according to claim 22, wherein said promoter is a tumor-specific promoter.

30. The composition according to claim 29, wherein said tumor-specific promoter is selected from the group consisting of TRP-1 promoter, HER2 promoter, HER3 promoter, ERBB2 promoter, ERBB3 promoter, CEA promoter, MUC1 promoter, α-fetoprotein promoter, pancreatic amylase promoter, tyrosinase related peptide promoter, and tumor rejection antigen precursor promoter.

31. The composition according to claim 22, wherein said promoter is a constitutive promoter.

32. The composition according to claim 31, wherein said constitutive promoter is selected from the group consisting of villin gene promoter, Rous sarcoma virus long terminal repeat, cytomegalovirus promoter, murine leukemia long terminal repeat, simian virus 40 early and late promoters, and herpes simplex virus thymidine kinase promoter.

33. The composition according to claim 22, wherein the polynucleotide is a mammalian polynucleotide.

34. The composition according to claim 33, wherein the polynucleotide is a human polynucleotide.

35. The composition according to claim 34, wherein the polynucleotide encodes CYP1A2.

36. The composition according to claim 22, wherein the polynucleotide is of rodent origin.

37. The composition according to claim 22, further comprising at least one agent capable of modulating glutathione level in a mammal, wherein the agent is methionine or acetylcysteine.

38. The composition according to claim 37, further comprising a pharmaceutically acceptable excipient, carrier or diluent.

39. The method for selectively killing cells in a mammal, the method comprising, concurrently or in sequence
  i) administering directly to the cells an effective amount of at least one vector comprising a promoter operably linked to a polynucleotide encoding a polypeptide selected from the group consisting of Cytochrome P450 1A2 (CYP1A2), Cytochrome P450 2E1 (CYP2E1), and Cytochrome P450 3A4 (CYP3A4), wherein said polypeptide is expressed in an effective amount to convert acetaminophen to a cytotoxic molecule; and
  ii) administering to the mammal an effective amount of acetaminophen,
  wherein the acetaminophen is converted in the cells into NABQI and wherein said cells do not express a sufficient level of glutathione to detoxify the NABQI.

* * * * *

SEQUENCE LISTING

```
<160> NUMBER OF SEQ ID NOS: 1

<210> SEQ ID NO 1
<211> LENGTH: 4214
<212> TYPE: DNA
<213> ORGANISM: Artificial Sequence
<220> FEATURE:
<223> OTHER INFORMATION: Description of Artificial Sequence: Base vector
      sequence  pEFPlink 6

<400> SEQUENCE: 1
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagaccatgg agcagaagct gatttccgag gaggacctgg     300
gatccgaatt caagcttccc ggggtcgaca tcgattagac tagtctagac ggcggcggca     360
gcttggctgt tttggcggat gagagaagat tttcagcctg atacagatta aatcagaacg     420
cagaagcggt ctgataaaac agaatttgcc tggcggcagt agcgcggtgg tcccacctga     480
ccccatgccg aactcagaag tgaaacgccg tagcgccgat ggtagtgtgg ggtctcccca     540
tgcgagagta gggaactgcc aggcatcaaa taaaacgaaa ggctcagtcg aaagactggg     600
```

-continued

```
cctttcgttt tatctgttgt ttgtcggtga acgctctcct gagtaggaca aatccgccgg      660
gagcggattt gaacgttgcg aagcaacggc ccggagggtg gcgggcagga cgcccgccat      720
aaactgccag gcatcaaatt aagcagaagg ccatcctgac ggatggcctt tttgcgtttc      780
tacaaactct ttttgtttat ttttctaaat acattcaaat atgtatccgc tcatgagaca      840
ataaccctga taaatgcttc aataatattg aaaaaggaag agtatgagta ttcaacattt      900
ccgtgtcgcc cttattccct tttttgcggc attttgcctt cctgttttg ctcacccaga       960
aacgctggtg aaagtaaaag atgctgaaga tcagttgggt gcacgagtgg gttacatcga     1020
actggatctc aacagcggta agatccttga gagttttcgc cccgaagaac gttttccaat     1080
gatgagcact tttaaagttc tgctatgtgg cgcggtatta cccgtgttg acgccgggca      1140
agagcaactc ggtcgccgca tacactattc tcagaatgac ttggttgagt actcaccagt     1200
cacagaaaag catcttacgg atggcatgac agtaagagaa ttatgcagtg ctgccataac     1260
catgagtgat aacactgcgg ccaacttact tctgacaacg atcggaggac cgaaggagct     1320
aaccgctttt ttgcacaaca tgggggatca tgtaactcgc cttgatcgtt gggaaccgga     1380
gctgaatgaa gccataccaa acgacgagcg tgacaccacg atgcctacag caatggcaac     1440
aacgttgcgc aaactattaa ctggcgaact acttactcta gcttcccggc aacaattaat     1500
agactggatg gaggcggata aagttgcagg accacttctg cgctcggccc ttccggctgg     1560
ctggtttatt gctgataaat ctggagccgg tgagcgtggg tctcgcggta tcattgcagc     1620
actggggcca gatggtaagc cctcccgtat cgtagttatc tacacgacgg ggagtcaggc     1680
aactatggat gaacgaaata gacagatcgc tgagataggt gcctcactga ttaagcattg     1740
gtaactgtca gaccaagttt actcatatat actttagatt gatttaaaac ttcatttta     1800
atttaaaagg atctaggtga agatcctttt tgataatctc atgaccaaaa tcccttaacg     1860
tgagttttcg ttccactgag cgtcagaccc cgtagaaaag atcaaaggat cttcttgaga     1920
tccttttttt ctgcgcgtaa tctgctgctt gcaaacaaaa aaaccaccgc taccagcggt     1980
ggtttgtttg ccggatcaag agctaccaac tcttttttccg aaggtaactg gcttcagcag    2040
agcgcagata ccaaatactg tccttctagt gtagccgtag ttaggccacc acttcaagaa     2100
ctctgtagca ccgcctacat acctcgctct gctaatcctg ttaccagtgg ctgctgccag     2160
tggcgataag tcgtgtctta ccgggttgga ctcaagacga tagttaccgg ataaggcgca     2220
gcggtcgggc tgaacggggg gttcgtgcac acagcccagc ttggagcgaa cgacctacac     2280
cgaactgaga tacctacagc gtgagctatg agaaagcgcc acgcttcccg aagggagaaa     2340
ggcggacagg tatccggtaa gcggcagggt cggaacagga gagcgcacga gggagcttcc     2400
agggggaaac gcctggtatc tttatagtcc tgtcgggttt cgccacctct gacttgagcg     2460
tcgatttttg tgatgctcgt caggggggcg gagcctatgg aaaaacgcca gcaacgcggc     2520
cttttttacgg ttcctggcct tttgctggcc ttttgctcac atgttctttc ctgcgttatc    2580
ccctgattct gtggataacc gtattaccgc ctttgagtga gctgataccg ctcgccgcag     2640
ccgaacgacc gagcgcagcg agtcagtgag cgaggaagcg gaagagcgcc tgatgcgta     2700
ttttctcctt acgcatctgt gcggtatttc acaccgcata tggtgcactc tcagtacaat     2760
ctgctctgat gccgcatagt taagccagta tacactccgc tatcgctacg tgactgggtc     2820
atggctgcgc cccgacaccc gccaacaccc gctgacgcgc cctgacgggc ttgtctgctc     2880
ccggcatccg cttacagaca agctgtgacc gtctccggga gctgcatgtg tcagaggttt     2940
tcaccgtcat caccgaaacg cgcgaggcag cagatcaatt cgcgcgcgaa ggcgaagcgg     3000
```

```
catgcattta cgttgacacc atcgaatggt gcaaaacctt tcgcggtatg gcatgatagc   3060
gcccggaaga gagtcaattc agggtggtga atgtgaaacc agtaacgtta tacgatgtcg   3120
cagagtatgc cggtgtctct tatcagaccg tttcccgcgt ggtgaaccag gccagccacg   3180
tttctgcgaa aacgcgggaa aaagtggaag cggcgatggc ggagctgaat tacattccca   3240
accgcgtggc acaacaactg gcgggcaaac agtcgttgct gattggcgtt gccacctcca   3300
gtctggccct gcacgcgccg tcgcaaattg tcgcggcgat taaatctcgc gccgatcaac   3360
tgggtgccag cgtggtggtg tcgatggtag aacgaagcgg cgtcgaagcc tgtaaagcgg   3420
cggtgcacaa tcttctcgcg caacgcgtca gtgggctgat cattaactat ccgctggatg   3480
accaggatgc cattgctgtg gaagctgcct gcactaatgt tccggcgtta tttcttgatg   3540
tctctgacca gacacccatc aacagtatta ttttctccca tgaagacggt acgcgactgg   3600
gcgtggagca tctggtcgca ttgggtcacc agcaaatcgc gctgttagcg ggcccattaa   3660
gttctgtctc ggcgcgtctg cgtctggctg gctggcataa atatctcact cgcaatcaaa   3720
ttcagccgat agcggaacgg gaaggcgact ggagtgccat gtccggtttt caacaaacca   3780
tgcaaatgct gaatgagggc atcgttccca ctgcgatgct ggttgccaac gatcagatgg   3840
cgctgggcgc aatgcgcgcc attaccgagt ccgggctgcg cgttggtgcg gatatctcgg   3900
tagtgggata cgacgatacc gaagacagct catgttatat cccgccgtta accaccatca   3960
aacaggattt tcgcctgctg gggcaaacca gcgtggaccg cttgctgcaa ctctctcagg   4020
gccaggcggt gaagggcaat cagctgttgc ccgtctcact ggtgaaaaga aaaccaccc    4080 tggcgcccaa tacgcaaacc gcctctcccc gcgcgttggc cgattcatta atgcagctgg   4140
cacgacaggt ttcccgactg gaaagcgggc agtgagcgca acgcaattaa tgtgagttag   4200
cgcgaattga tctg                                                     4214
```